United States Patent
Kahana et al.

(10) Patent No.: US 9,939,565 B2
(45) Date of Patent: *Apr. 10, 2018

(54) REFLECTIVE ELEMENT FOR FIBER OPTIC SENSOR

(71) Applicant: Qualitrol Company LLC, Fairport, NY (US)

(72) Inventors: Yuvi Kahana, Rinatya (IL); Alexander Kots, Ashdod (IL); Alexander Paritsky, Modiin (IL)

(73) Assignee: Qualitrol Company LLC, Fairport, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/670,691

(22) Filed: Mar. 27, 2015

(65) Prior Publication Data

US 2015/0346399 A1  Dec. 3, 2015

Related U.S. Application Data

(63) Continuation of application No. 14/287,361, filed on May 27, 2014, now Pat. No. 8,995,798.

(51) Int. Cl.
| | |
|---|---|
| *G02B 6/00* | (2006.01) |
| *G02B 5/09* | (2006.01) |
| *G01D 5/26* | (2006.01) |
| *G01K 5/56* | (2006.01) |
| *G01N 21/47* | (2006.01) |
| *G02B 1/02* | (2006.01) |

(Continued)

(52) U.S. Cl.
CPC ............... *G02B 5/09* (2013.01); *G01D 5/268* (2013.01); *G01K 5/56* (2013.01); *G01K 5/62* (2013.01); *G01N 21/47* (2013.01); *G02B 1/02* (2013.01); *G02B 6/262* (2013.01); *G01N 2021/4709* (2013.01); *G01N 2201/088* (2013.01); *G01N 2201/0873* (2013.01)

(58) Field of Classification Search
None
See application file for complete search history.

(56) References Cited

U.S. PATENT DOCUMENTS

| | | |
|---|---|---|
| 4,414,471 A | 11/1983 | Rines |
| 4,915,882 A | 4/1990 | Wisotzki |

(Continued)

OTHER PUBLICATIONS

U.S. Appl. No. 13/935,955, filed Jul. 5, 2014, and entitled Fiber Optic Accelerometer.

(Continued)

*Primary Examiner* — Tina Wong
(74) *Attorney, Agent, or Firm* — Seed IP Law Group LLP

(57) ABSTRACT

A reflective element for directing an optical signal into a fiber optic sensor having an optical fiber includes a plane containing a sharply defined straight line that separates between a first area of low reflectivity and a second area of high reflectivity. The plane is disposed parallel to a free end surface of the optical fiber so that the free end surface intersects the line of the reflective element, whereby relative movement between the free end surface of the optical fiber and the line in response to a physical change sensed by the fiber optic sensor induces variations in an optical signal reflected by the reflective element through the optical fiber, which variations allow measurement of the physical change.

20 Claims, 4 Drawing Sheets

(51) Int. Cl.
*G02B 6/26* (2006.01)
*G01K 5/62* (2006.01)

(56) References Cited

U.S. PATENT DOCUMENTS

| | | | |
|---|---|---|---|
| 5,276,322 A | 1/1994 | Carome | |
| 5,771,091 A | 6/1998 | Paritsky | |
| 6,744,940 B2 | 6/2004 | Kole | |
| 6,920,257 B1 | 7/2005 | Mekis | |
| 7,332,329 B2 | 2/2008 | Wark | |
| 7,583,866 B2 | 9/2009 | Huang | |
| 7,787,735 B2 * | 8/2010 | Fujiwara | B82Y 20/00 385/131 |
| 7,801,405 B2 | 9/2010 | Daum | |
| 7,931,867 B2 | 4/2011 | Korlach | |
| 8,432,552 B2 | 4/2013 | Gibler | |
| 2003/0113766 A1 | 6/2003 | Pepper | |
| 2004/0240779 A1 | 12/2004 | Yeh | |
| 2005/0158002 A1 | 7/2005 | Kubby | |
| 2007/0247613 A1 | 10/2007 | Cloustier | |
| 2008/0013878 A1 | 1/2008 | Fujiwara | |
| 2009/0123112 A1 | 5/2009 | Kahana | |
| 2010/0158440 A1 | 6/2010 | Kim | |

OTHER PUBLICATIONS

Non-Final Office Action dated Jan. 29, 2014 in U.S. Appl. No. 13/935,955.
Notice of Allowance and Fee(s) Due dated Mar. 10, 2014 in U.S. Appl. No. 13/935,955.
Non-Final Office Action dated Jan. 16, 2015 in U.S. Appl. No. 14/287,361.
Notice of Allowance and Fee(s) Due dated Feb. 11, 2015 in U.S. Appl. No. 14/287,361.
U.S. Appl. No. 14/287,361, filed May 27, 2014 entitled Reflective Element for Fiber Optic Sensor.

* cited by examiner

REFLECTIVE ELEMENT FOR FIBER OPTIC SENSOR

The present application is a continuation of U.S. patent application Ser. No. 14/287,361, filed May 27, 2014, and entitled REFLECTIVE ELEMENT FOR FIBER OPTIC SENSOR, the entirety of which is incorporated herein by reference.

1. THE FIELD OF THE INVENTION

The present invention relates to fiber optic sensors, particularly to sensors substantially not affected by very strong electromagnetic fields able to work in high temperature conditions.

2. BACKGROUND OF THE INVENTION

Fiber optic sensors are known that use light energy and optical fibers to sense different physical parameters such as pressure, temperature, acceleration etc. Most of them consist of light source, photo detector, one or few optical fibers, reflective target and a sensitive to a certain physical effects element someway attached to the optical fibers or reflective target. Via a transmitting optical fiber light from a light source is dispatched to reflective target that partly reflects it back through a receiving optical fiber to a photo detector. Under a certain physical effects a sensitive element changes the relative position of the optical fiber and reflective target thereby changing the intensity of light reflected by the target into receiving optical fiber and transformed by the photo detector into electrical signal. Some of the fiber optic sensors include only one optical fiber combining transmitting and receiving fibers in one. Examples of such sensors are disclosed in U.S. 2009/0123112, U.S. 2007/0247613 and U.S. Pat. No. 5,771,091.

The reflective target is the most exacting and thus most expensive part of these sensors. Even small distortions of its shape or degradation of its reflective surfaces caused by temperature variations can dramatically deteriorate the sensor characteristics.

U.S. Pat. No. 4,915,882 discloses a method for manufacturing uniformly smooth monocrystal reflectors of copper, silver or gold using a crucible polished to optical quality on the surface in contact with the reflecting surface of the monocrystal. It is noted that monocrystal reflectors withstand much better the extreme thermal loads caused by laser beams, but that the advantages inherent in the monocrystalline structure of the reflecting metal body are partially lost again during forming and/or machining as these operations modify the homogeneous crystalline texture. Reflection produced by monocrystal reflectors was found to be better for etched surfaces than in polished surfaces. Etched surfaces, however, are nonhomogeneous so that while of interest as protective shields against laser beams they do not lend themselves to optical or similar purposes in which a specific optical path requires a precisely defined reflecting surface.

U.S. Pat. No. 4,414,471 discloses sensing of acoustic waves achieved by providing spaced apart stationary and cantilevered optic fibers whereby inertial forces created by acoustic signals modulate an optical signal carried by the fibers through vibration of the cantilevered fiber. In one embodiment, the sensor includes a cantilevered beam mounted at the far end to a rigid structure and having a reflective member such as a concave mirror at the free end thereof. The end of optical fiber is disposed at the center of the sphere of which the mirror surface is a section. Light fed into the fiber is reflected from the mirror, received by the fiber and applied to a detector at. When acoustic waves are incident on the transducer they will cause vibration of the cantilevered beam due to inertial forces. The mirror attached to the beam also vibrates and amplitude modulates the light received by the mirror and returned to the fiber.

Our co-pending U.S. Ser. No. 13/935,955, whose contents are wholly incorporated herein by reference, discloses a fiber optic accelerometer comprising a cantilever section which moves upon vibration or acceleration of the accelerometer such that its position relative to a reflective target changes thereby reducing the instantaneous intensity of light reflected by the target into the second end of the optical fiber and measured by the photo detector. The reflective target is formed of an optical fiber stub having a first end proximate the free second end of the optical fiber and a second end remote therefrom.

In one embodiment, the first end of the optical fiber stub has a slanted surface formed at an angle to an optical axis of the optical fiber stub and the second end of the optical fiber stub is cut perpendicularly to the optical axis and is coated with a highly polished efficient light reflecting material.

In another embodiment, the first end of the optical fiber stub has a stepped cut so as to present a first surface portion closer to the end of the optical fiber and a more distant second surface section and the second end of the optical fiber stub is cut perpendicularly to said optical axis and is coated with a highly polished efficient light reflecting material.

In both cases, there is no change in reflectivity of the optical fiber stub, the variation in signal injected into the optical fiber being caused solely by the off-axis reflection of light from the optical fiber stub owing to the deflection of the cantilever such that movement of the free end of the optical fiber causes a lessor or greater amount of the reflected light to be captured by the free end of the optical fiber. The same is true in U.S. Pat. No. 4,414,471 where the concave mirror reflects light into the cantilever regardless of its deflection, the vibration of the mirror serving to modulate the light prior to its reflection into the free end of the fiber.

BRIEF SUMMARY OF THE INVENTION

It is an object of the present invention to provide a reflective element for fiber optic sensors possessing in some cases sensitivity to a certain physical effects and having a simpler construction, and being low cost for its production.

This object is realized in accordance with the invention by a reflective element for a fiber optic sensor having the features of the respective independent claims.

The invention provides a reflective element for a fiber optic sensor based on a single optical fiber, said reflective element comprising a plane containing a sharply defined straight line that separates between a first area of low reflectivity and a second area of high reflectivity, said plane being disposed parallel to a free end surface of the optical fiber so that said free end surface intersects said line, whereby relative movement between the free end surface of the optical fiber and the line in response to a physical change sensed by the fiber optic sensor induces variations in an optical signal reflected by the reflective element through the optical fiber, said variations allowing measurement of the physical change.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1b and 1c are graphical representations showing intensity of a series of optical pulses directed to the free end of the fiber optic sensor of FIG. 1a;

FIGS. 2a and 2b show schematically a respective cross-section and end elevation of a reflective element for a single axis fiber optic sensor based on a single fiber;

DETAILED DESCRIPTION OF EMBODIMENTS

In the following description of some embodiments, identical components that appear in more than one figure or that share similar functionality will be referenced by identical reference symbols.

Figure 1A:
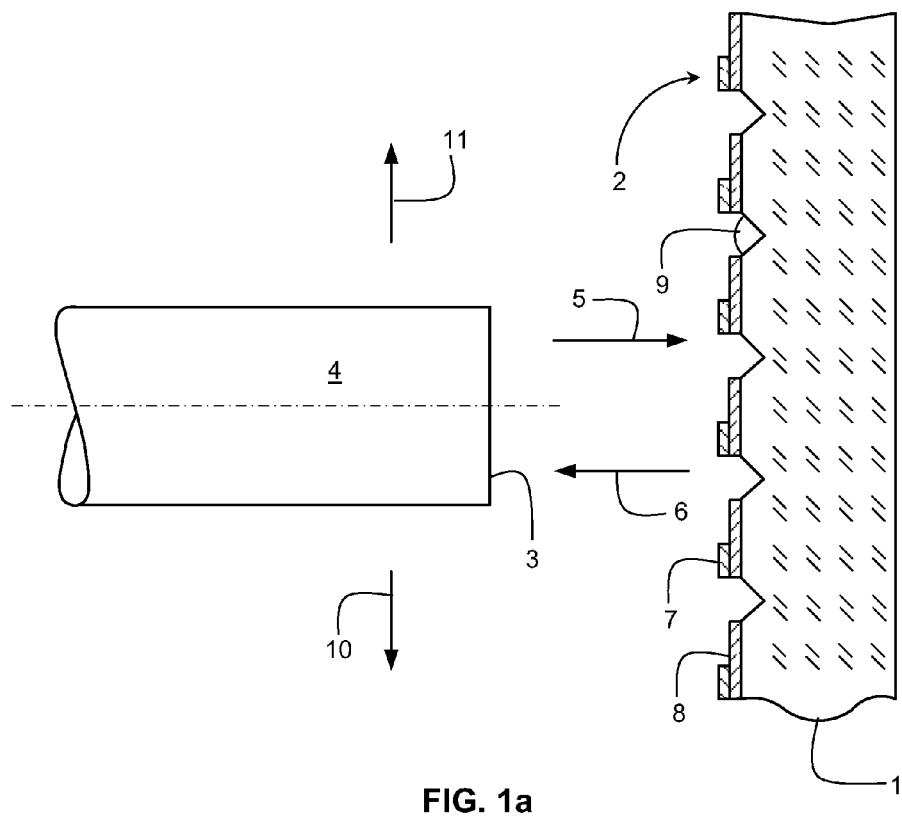
FIG. 1a shows schematically the construction of a reflective element for a digital fiber optic sensor made of monocrystal material by technology of anisotropic etching and vapor deposition.
Figure 1B:
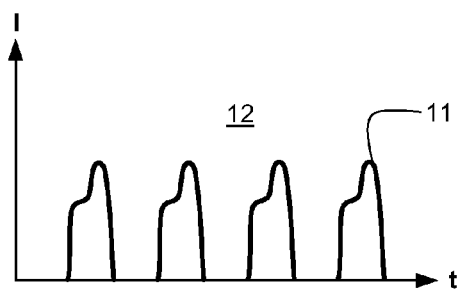
Figure 1C:
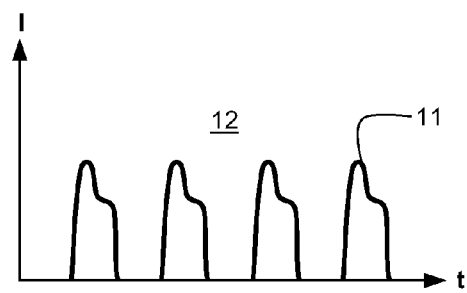

FIG. 1a is a schematic cross-section showing construction of a reflective element for a fiber optic sensor. The reflective element may be a plate made of mono-crystal material 1 with multiple parallel reflective stripes 2 disposed on the side faced to the free end 3 of an optical fiber 4 and separated by v-grooves. The v-grooves define lines separating the areas of high reflectivity from the areas of low reflectivity. The optical fiber 4 emits light 5 toward the reflective element and collects the back reflected light 6. Each reflective stripe 2 comprises an uppermost reflective surface 7 deposited on a substrate layer 8 by vapor deposition or sputtering. The reflective surface 7 may be formed of a material having high reflectivity such as gold while the substrate layer 8 may be formed of a material having medium reflectivity such as platinum or nickel such that the respective reflectivity of the two layers is different. The v-grooves are made by wet anisotropic etching. The angle θ between the opposing faces of the v-grooves depends of the selected mono-crystal material and should be no greater than 70°. In this case the intensity of light reflected in the direction of the free end of the optical fiber will be close to zero. Thus when, under a given physical load, the optical fiber 4 is displaced in the direction 10 relative to the reflective element and its free end 3 intersects the lines between adjacent areas of high and low reflectivity, the intensity of the reflected light collected by the free end 3 of the optical fiber 4 appears in the time domain 12 as a series of pulses having an asymmetrical profile 13 as shown in FIG. 1b. When the optical fiber 4 is displaced in the reverse direction 11, the profile of the pulses in the time domain will be of inverse shape as shown in FIG. 1c. So the number of pulses and the shape of their profile define the magnitude and direction of optical fiber displacement. Such a reflective element may be used for direct digitization of a fiber optic sensor output signal.

Figure 2B:
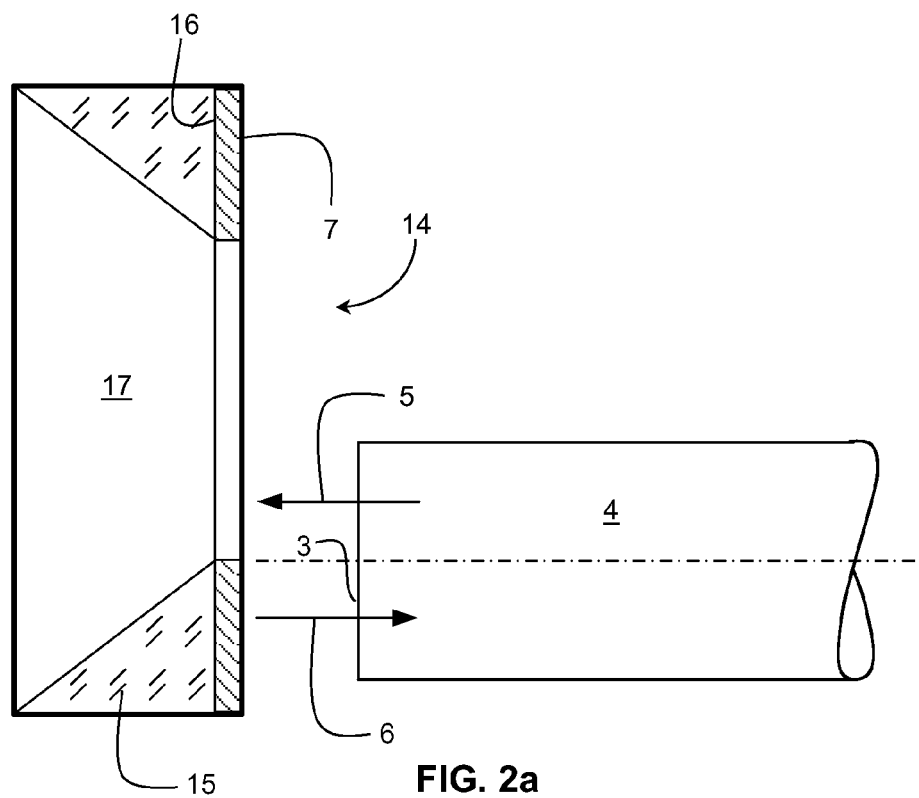

FIG. 2a shows schematically a partial cross-sectional view of a reflective element 14 for a single axis fiber optic sensor based on one optical fiber 4 wherein the reflective element has the shape of flat hollow frame made of monocrystalline material 15 with one face 16 coated with a highly polished, efficient light reflecting material such as gold so as to form a good reflecting surface 7. The internal edges of the aperture are beveled to form a truncated square pyramidal shaped aperture 17 with the base of the pyramid remote from the reflective face. The aperture is preferably formed by means of anisotropic wet etching, whereby the internal edges 18 and 19 are formed absolutely straight and strictly orthogonal to each other. The classic approach is by etching a hole in <100> silicon wafer using a chemical such as potassium hydroxide. The result is a square pyramidal shape aperture. The selected reflective material may be deposited by vapor deposition technology. Both of these technologies are well-suited to mass production enabling the manufacturing price of so delicate and precise a component to be dramatically reduced. The free end 3 of the optical fiber 4 emits light 5 in the direction of the reflective element and collects the reflected light 6. Only movement of the free fiber end 3 in a direction perpendicular to the edge 19 shown in FIG. 2b can produce variation of intensity of the reflected light and thus the valuable signal while movement in the parallel direction to the edge 19 cannot. Thus the reflective element produces a spatial filtration of a fiber movement making the fiber optic sensor sensitive to a given physical effect such as acceleration, transverse force, deformation, etc. in only one direction.

Figure 2B:
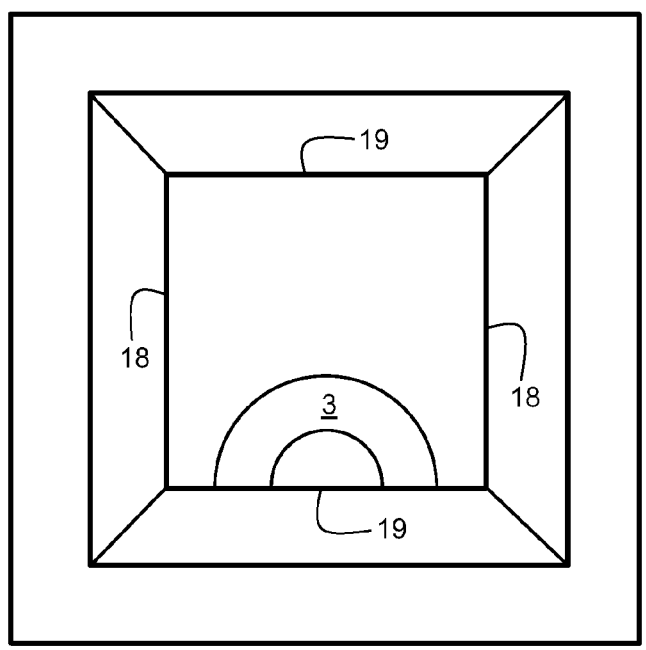
Figure 3:
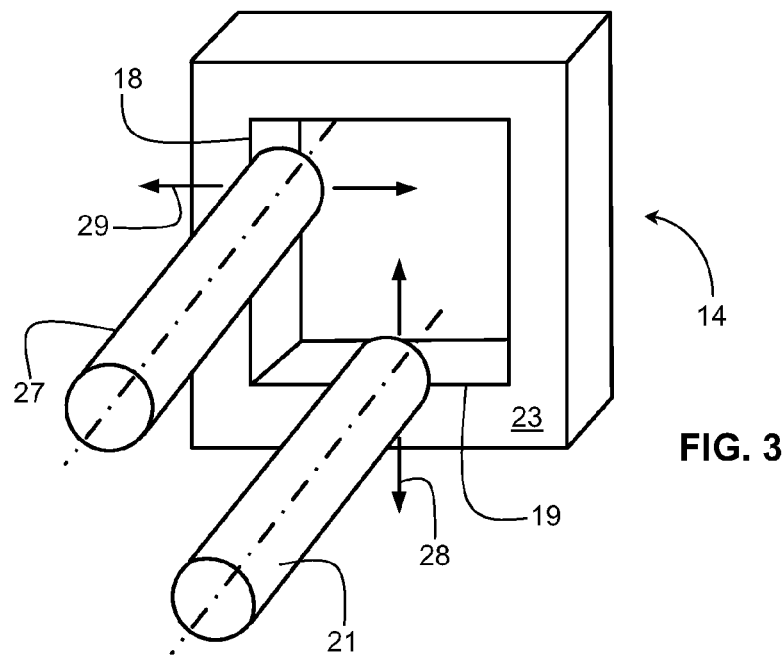
FIG. 3 is a schematic view of a dual axis fiber optic sensor having two independent fibers and a single reflective element similar to that depicted in FIG. 2.

FIG. 3 is a schematic view of a dual axis fiber optic sensor employing the reflective element 14 depicted in FIG. 2 in combination with two independent optical fibers 21 and 27 capable of displacement in random directions under a given physical load. The free ends of both fibers are respectively mounted proximate the internal orthogonal edges 18 and 19 of the reflective element 14. Thus the reflective element produces a spatial filtration of movement of the two fibers simultaneously making the fiber optic sensor sensitive to physical effects such as acceleration, transverse force, deformation, etc. in two strictly orthogonal directions as shown by the arrows 28, 29.

In the embodiments described so far, the sensor signal is obtained upon movement of the optical fiber in a direction that is perpendicular to a fixed edge of the reflective element. Only the optical fiber moves with the surface of its free end being substantially parallel to the highly reflective surface of the reflective element, which does not move. However, the equivalent effect can be achieved using other configurations wherein the reflective element itself moves in response to an applied force. In some embodiments movement of the reflective element induces movement of the free end of the optical fiber, while still retaining some relative movement with an edge of the reflective element. In other embodiments, the free end of the optical fiber remains fixed in space so that the required relative movement with an edge of the reflective element is induced by motion of the reflective element only. Non-limiting examples of these embodiments will now be described.

Figure 4A:
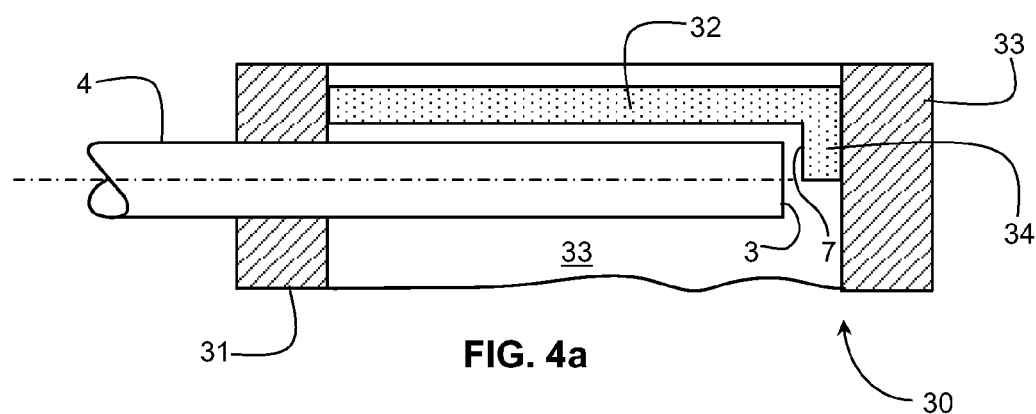
FIGS. 4a and 4b show schematically a reflective element for a fiber optic pressure sensor in an initial and subsequent deflected state, respectively.
Figure 4B:
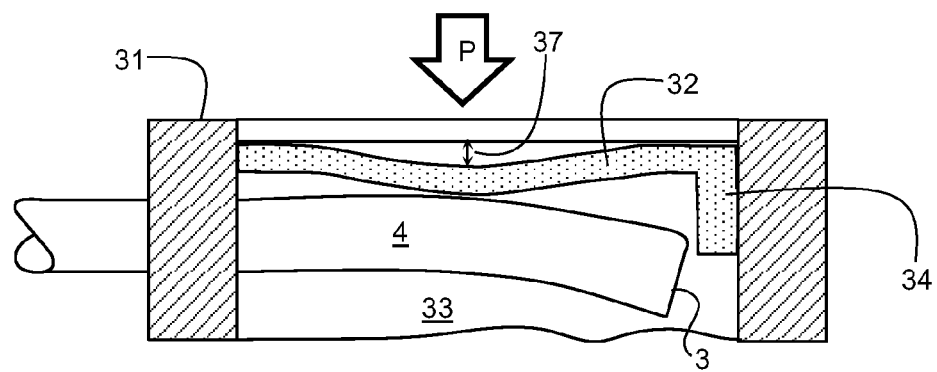

FIG. 4a shows a schematic cross section of a fiber optic pressure sensor 30 having a sensor housing 31 supporting the optical fiber 4 and wherein a reflective element is formed as a generally L-shaped diaphragm 32 sealing a channel 33 in the sensor housing 31. The diaphragm 32 is formed by wet processing of mono crystal material and has a generally elongate body portion that spans the width of the channel 33 terminating at an end of the channel proximate the free end of the optical fiber 4 in a stepped portion 34 whose height is about half the diameter of the optical fiber 4. The internal face of the stepped portion 34 is coated with a highly polished efficient light reflecting material so as to form a reflective surface 7. The optical fiber represents a cantilever beam that passes beneath a membrane parallel to its plane and under its center on the minimal distance from its inner surface. The optical fiber 4 conveys the light from a source of light (not shown) to the reflective surface 7 and conveys the reflected light back to a photodetector (not shown). Under applied force, P, the diaphragm is deflected by a deflection 37 as a function of applied force thereby applying a bending force to the optical fiber 4 and changing the position of its free end relative to the reflective stepped portion 34 (FIG. 4*b*). Consequently, the intensity of light conveyed to the photodetector will also change proportional to the applied force, P.

Figure 5:
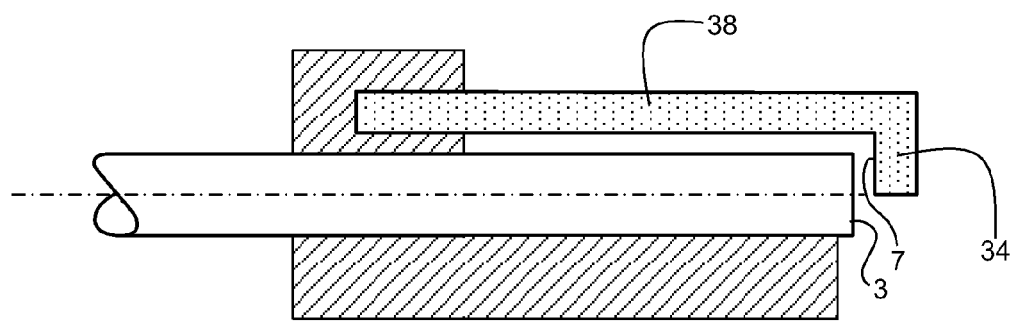
FIG. 5 shows a schematic view of a reflective element for a fiber dynamometer made of mono crystal material.

FIG. 5 shows a schematic cross section of a reflective element in the shape of cantilever beam 38 for a fiber optic dynamometer wherein the beam 38 is made of mono crystal material by wet etching with a stepped portion 34 on its free end coated by a highly reflective material to form a reflecting surface 7. Under applied force 39 the beam 38 bends and thus changes the position of the reflective stepped portion 34 relative to the free end 3 of the optical fiber 4. Consequently, the intensity of light conveyed to photodetector will also change proportional to the applied force. The cantilever beam defines an elongated surface that is perpendicular to an internal face of the stepped portion 34 and to which an applied force induces deflection of the stepped portion 34 relative to the free end 3 of the optical fiber 4.

Figure 6:
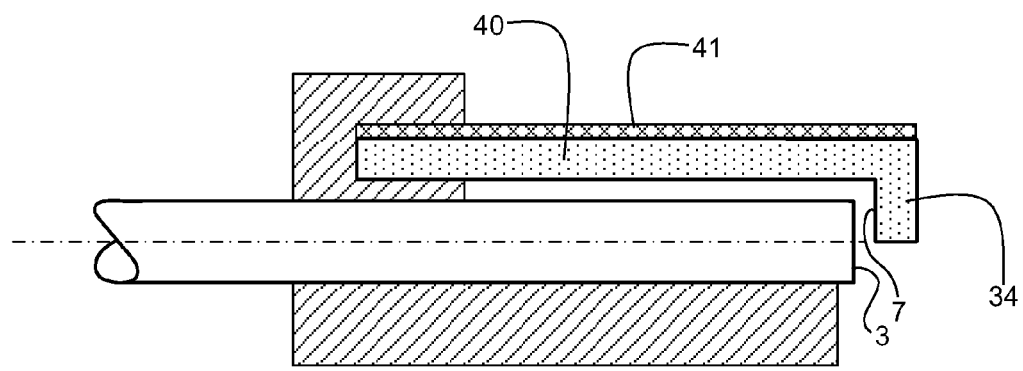
FIG. 6 shows a schematic view of a reflective element for a fiber optic temperature sensor made of mono crystal material.

FIG. 6 shows a schematic cross section of reflective element in the shape of cantilever beam 40 for a fiber optic thermometer wherein the beam 40 is made of mono crystal material by wet etching with a stepped portion 34 on its free end coated by a highly reflective material to form a reflecting surface 7. One side of the beam 40 is coated with a layer of material 41 characterized by a coefficient of thermal expansion (CTE) that is very different from that of the mono crystal material of which the beam 40 is formed. At ambient temperature variations, the beam 40 bends and thus changes the position of the reflective stepped portion 34 relative to the free end 3 of the optical fiber 4. Consequently, the intensity of light conveyed to photodetector will also change proportional to ambient temperature change.

In the embodiment of FIG. 6, the cantilever beam defines an elongated surface that is perpendicular to an internal face of the stepped portion 34 and that supports the layer of material 41. Typically, the layer of material 41 is coated on the elongated surface of the beam. But it could equally well be riveted or attached thereto using adhesive as in known per se.

The invention claimed is:

1. A reflective element for a fiber optic sensor based on a single optical fiber, said reflective element comprising a plane containing a sharply defined edge that separates between a first area of low reflectivity and a second area of high reflectivity, said plane being disposed parallel to a free end surface of the optical fiber so that said free end surface intersects said edge, whereby relative movement between the free end surface of the optical fiber and the edge in response to a physical change sensed by the fiber optic sensor induces variations in an optical signal reflected by the reflective element through the optical fiber, said variations allowing measurement of the physical change; and multiple abutting areas of respective high and low reflectivity each separated by respective sharply defined straight edges that are intermittently intersected by the free end surface of the optical fiber in response to said physical change, wherein the reflective element comprises a plate supporting multiple parallel reflective stripes of reflectivity and intermediate v-grooves of low reflectivity, wherein the reflective element is formed of mono-crystal material.

2. The reflective element according to claim 1, wherein the reflective stripes are deposited on a substrate layer of low reflectivity using vapor deposition technology.

3. The reflective element according to claim 1, wherein the stripe is gold and the substrate is platinum or nickel.

4. The reflective element according to claim 1, wherein the v-grooves are formed by wet anisotropic etching.

5. The reflective element according to claim 1, wherein an internal angle between opposing faces of the v-grooves is no greater than 70°.

6. The reflective element according to claim 1, wherein the reflective stripes are metal layers of submicron thickness made by vapor deposition or sputtering.

7. The reflective element according to claim 1, comprising a generally L-shaped diaphragm having an elongate body portion and a stepped portion that defines an internal face that is coated with a highly polished efficient light reflecting material so as to form a reflective surface.

8. The reflective element according to claim 7, being formed by anisotropic wet etching.

9. The reflective element according to claim 7, wherein a height of the internal face of the step is approximately half a diameter of the optical fiber.

10. The reflective element according to claim 1, wherein the reflective element is a cantilever beam having on a free end thereof a step having an internal face coated by a highly reflective material that at least partially intersects the free end surface of the optical fiber, and wherein an elongated surface of the cantilever beam perpendicular to said internal face supports a layer of material having a different coefficient of thermal expansion to that of the cantilever beam, whereby a variation in ambient temperature induces the beam to bend and thus moves the step relative to the free end of the optical fiber.

11. The reflective element according to claim 10, being formed by anisotropic wet etching.

12. The reflective element according to claim 10, wherein a height of the internal face of the step is approximately half a diameter of the optical fiber.

13. A reflective element for a fiber optic sensor based on a single optical fiber, said reflective element comprising a plane containing a sharply defined edge that separates between a first area of low reflectivity and a second area of high reflectivity, said plane being disposed parallel to a free end surface of the optical fiber so that said free end surface intersects said edge, whereby relative movement between the free end surface of the optical fiber and the edge in response to a physical change sensed by the fiber optic sensor induces variations in an optical signal reflected by the reflective element through the optical fiber, said variations allowing measurement of the physical change; and multiple abutting areas of respective high and low reflectivity each separated by respective sharply defined straight edges that are intermittently intersected by the free end surface of the optical fiber in response to said physical change, wherein the reflective element comprises a plate supporting multiple parallel reflective stripes of reflectivity and intermediate v-grooves of low reflectivity, wherein:
said plane includes an aperture having a shape of a truncated square pyramid, a base of which is behind the plane; and
at least one edge of the aperture functions as said sharply defined edge that separates between the first area of low reflectivity constituted by the aperture and the second area of high reflectivity constituted by the plane surrounding the aperture.

14. The reflective element according to claim 13, being formed of mono-crystal material.

15. The reflective element according to claim 13, wherein the aperture is formed by wet anisotropic etching.

16. The reflective element according to claim 13, wherein the second area of high reflectivity is formed of metal layers of submicron thickness made by vapor deposition or sputtering.

17. The reflective element according to claim 13, wherein two mutually perpendicular edges of said aperture are configured for disposing in spaced relationship with respective optical fibers configured for independent displacement in random directions under an applied physical force.

18. A reflective element for a fiber optic sensor based on a single optical fiber, said reflective element comprising a plane containing a sharply defined edge that separates between a first area of low reflectivity and a second area of high reflectivity, said plane being disposed parallel to a free end surface of the optical fiber so that said free end surface intersects said edge, whereby relative movement between the free end surface of the optical fiber and the edge in response to a physical change sensed by the fiber optic sensor induces variations in an optical signal reflected by the reflective element through the optical fiber, said variations allowing measurement of the physical change,
wherein the reflective element is a cantilever beam formed of mono-crystal material and having on a free end thereof a step having an internal face coated by a highly reflective material that at least partially intersects the free end surface of the optical fiber.

19. The reflective element according to claim 18, being formed by anisotropic wet etching.

20. The reflective element according to claim 18, wherein a height of the internal face of the step is approximately half a diameter of the optical fiber.

* * * * *